(12) United States Patent
Pruter

(10) Patent No.: US 7,837,627 B1
(45) Date of Patent: *Nov. 23, 2010

(54) SHEATH APPARATUS FOR GUIDING NEEDLES FOR USE WITH A MEDICAL ULTRASOUND TRANSCEIVER

(76) Inventor: Rick L Pruter, 21 Woodcrest La. NE., Iowa City, IA (US) 52240

( * ) Notice: Subject to any disclaimer, the term of this patent is extended or adjusted under 35 U.S.C. 154(b) by 918 days.

This patent is subject to a terminal disclaimer.

(21) Appl. No.: 10/907,366

(22) Filed: Mar. 30, 2005

Related U.S. Application Data

(63) Continuation-in-part of application No. 10/063,753, filed on May 10, 2002, now Pat. No. 6,908,433.

(60) Provisional application No. 60/575,672, filed on May 28, 2004.

(51) Int. Cl.
*A61B 8/00* (2006.01)
(52) U.S. Cl. .................. 600/461; 604/117; 604/272
(58) Field of Classification Search .................. 600/437, 600/466, 461, 459, 464; 604/117, 272
See application file for complete search history.

(56) References Cited

U.S. PATENT DOCUMENTS

| | | | |
|---|---|---|---|
| 4,151,834 A * | 5/1979 | Sato et al. ................... | 600/446 |
| 4,469,106 A * | 9/1984 | Harui ......................... | 600/461 |
| 4,567,895 A * | 2/1986 | Putzke ........................ | 600/445 |
| 4,567,896 A * | 2/1986 | Barnea et al. ............... | 600/443 |
| 4,742,829 A | 5/1988 | Law et al. | |
| 4,838,506 A | 6/1989 | Cooper | |
| 4,865,590 A * | 9/1989 | Marmar ...................... | 604/180 |
| 4,877,033 A | 10/1989 | Seitz, Jr. | |
| 4,883,059 A | 11/1989 | Stedman et al. | |
| 4,911,173 A | 3/1990 | Terwilliger | |
| 5,052,396 A | 10/1991 | Wedel et al. | |
| 5,088,178 A | 2/1992 | Stolk | |
| 5,088,500 A | 2/1992 | Wedel et al. | |
| 5,090,414 A | 2/1992 | Takano | |
| 5,166,073 A * | 11/1992 | Lefkowitz et al. ............. | 436/57 |

(Continued)

FOREIGN PATENT DOCUMENTS

WO    WO 99/34735    7/1999

OTHER PUBLICATIONS

"Solutions for Ultrasound" brochure from CIVCO Meedical Instruments Co., Medical Parkway, 102 Highway 1 South, Kalona, Iowa 52247.

*Primary Examiner*—Brian Casler
*Assistant Examiner*—Amanda Lauritzen
(74) *Attorney, Agent, or Firm*—Simmons Perrine Moyer Bergman PLC

(57) ABSTRACT

An apparatus and method for guiding a needle where a structure is disposed on an exterior of a sterile sheath to aid in guiding the needle with respect to the transceiver, which transceiver is not yet inserted into the sterile sheath. In one case, the needle guide is attached to the exterior of the sheath; in another, a needle guide adapter is attached to the exterior of the sheath; in still another, an adhesive is attached on the inside of the sheath to assist in attachment with the transceiver. In still another, a temporary adhesive cover is attached to the internal adhesive and is removable upon full insertion of the transceiver into the sheath.

10 Claims, 6 Drawing Sheets

U.S. PATENT DOCUMENTS

| | | |
|---|---|---|
| 5,235,987 A | 8/1993 | Wolfe |
| 5,261,409 A * | 11/1993 | Dardel ............... 600/461 |
| 5,469,853 A * | 11/1995 | Law et al. ............ 600/463 |
| 5,490,522 A * | 2/1996 | Dardel ............... 600/461 |
| 5,623,931 A * | 4/1997 | Wung et al. .......... 600/461 |
| 5,758,650 A * | 6/1998 | Miller et al. ......... 600/461 |
| 5,910,113 A * | 6/1999 | Pruter ............... 600/437 |
| 5,941,889 A * | 8/1999 | Cermak .............. 606/130 |
| 5,968,016 A | 10/1999 | Yerfino et al. |
| 5,997,481 A * | 12/1999 | Adams et al. ......... 600/459 |
| D424,693 S | 5/2000 | Pruter |
| 6,102,867 A | 8/2000 | Dietz et al. |
| 6,200,312 B1 * | 3/2001 | Zikorus et al. ........ 606/32 |
| 6,251,073 B1 * | 6/2001 | Imran et al. .......... 600/443 |
| 6,296,614 B1 * | 10/2001 | Pruter ............... 600/461 |
| 6,361,499 B1 | 3/2002 | Bates et al. |
| 6,371,968 B1 | 4/2002 | Kogasaka et al. |
| 6,379,307 B1 * | 4/2002 | Filly et al. .......... 600/461 |
| 6,475,152 B1 * | 11/2002 | Kelly et al. .......... 600/461 |
| 6,743,177 B2 * | 6/2004 | Ito .................. 600/461 |
| 6,755,789 B2 * | 6/2004 | Stringer et al. ....... 600/461 |
| 7,087,024 B1 * | 8/2006 | Pruter ............... 600/461 |
| 2005/0059891 A1 * | 3/2005 | Kosaku .............. 600/439 |
| 2006/0058680 A1 * | 3/2006 | Solomon ............. 600/466 |
| 2006/0129046 A1 * | 6/2006 | Stevens et al. ........ 600/464 |
| 2006/0184035 A1 * | 8/2006 | Kimura et al. ........ 600/466 |
| 2007/0276253 A1 * | 11/2007 | Park et al. ........... 600/461 |

* cited by examiner

SHEATH APPARATUS FOR GUIDING NEEDLES FOR USE WITH A MEDICAL ULTRASOUND TRANSCEIVER

CROSS REFERENCE TO RELATED APPLICATIONS

This application is a continuation-in-part of an application entitled Adhesive method and apparatus for guiding needles filed by Rick L. Pruter on May 10, 2002, having Ser. No. 10/063,753, and it claims the benefit of a provisional patent application entitled "Method and system for assisting vascular intubation with a medical imaging transceiver", having Ser. No. 60/575,672, which was filed by Rick L. Pruter on May 28, 2004.

FIELD OF THE INVENTION

The present invention generally relates to needle guides for medical imaging transceivers, and more particularly relates to a universal needle guide for medical imaging transceivers which permit attachment to a medical imaging transceiver, independent of model.

BACKGROUND OF THE INVENTION

In recent years, hand-held medical imaging transceivers, such as ultrasound and gamma ray transceivers, have been used extensively for various medical imaging situations. Many clinics will use multiple transceivers. Some handheld transceivers are designed for external use, while trans-rectal and trans-vaginal transceivers are designed for use within body cavities.

In the past, each type of transceiver may require a different needle guide and/or a different mounting bracket to which a needle guide is attached. With numerous transceivers and numerous needle guide brackets, a medical imaging professional may become confused and frustrated as to what needle guide goes with which bracket and which transceiver, thereby reducing the efficiency of operations of the clinic.

Consequently, there exists a need for improved methods and apparatus for guiding needles in an efficient manner.

SUMMARY OF THE INVENTION

It is an object of the present invention to provide an apparatus and method for guiding a needle in an efficient manner.

It is a feature of the present invention to utilize a sterile sheath with an internal adhesive for affixing to a transceiver.

It is another feature of the present invention to include a removable internal adhesive cover inside said sterile sheath to facilitate ease of insertion of a medical imaging transceiver therein.

It is another feature of the present invention to include a sterile sheath with a needle guide attached thereto.

It is another feature of the present invention to include a needle guide adapter bracket attached to the sterile sheath.

It is an advantage of the present invention to achieve improved efficiency in guiding needles.

It is another feature of the present invention to have interlocking attachments disposed on an outside of a sheath.

It is another advantage of the present invention to provide for a common base sheath and various attachments for differing types of applications.

It is another feature of the present invention to include a hand-held display for locating veins.

It is another advantage to provide quick and easy deployment of equipment to be used to locate a vein.

The present invention is an apparatus and method for guiding needles designed to satisfy the aforementioned needs, provide the previously stated objects, include the above-listed features, and achieve the already articulated advantages. The present invention is carried out in a "technician burden-less" manner in a sense that the burden on a medical imaging of coupling one of a multiple of needle guides with one of a multiple of mounting brackets for one of a multiple of transceivers, has been greatly reduced.

Accordingly, the present invention is an apparatus and method including a sterile sheath which has a structure coupled thereto for assisting in affixing a needle guide to a transceiver. The present invention is also an apparatus for interlocking various pieces to an exterior of a common base sheath. The present invention is also a hand-held display apparatus for locating veins.

BRIEF DESCRIPTION OF THE DRAWINGS

The invention may be more fully understood by reading the following description of the preferred embodiments of the invention, in conjunction with the appended drawings wherein.

DETAILED DESCRIPTION

Figure 1:
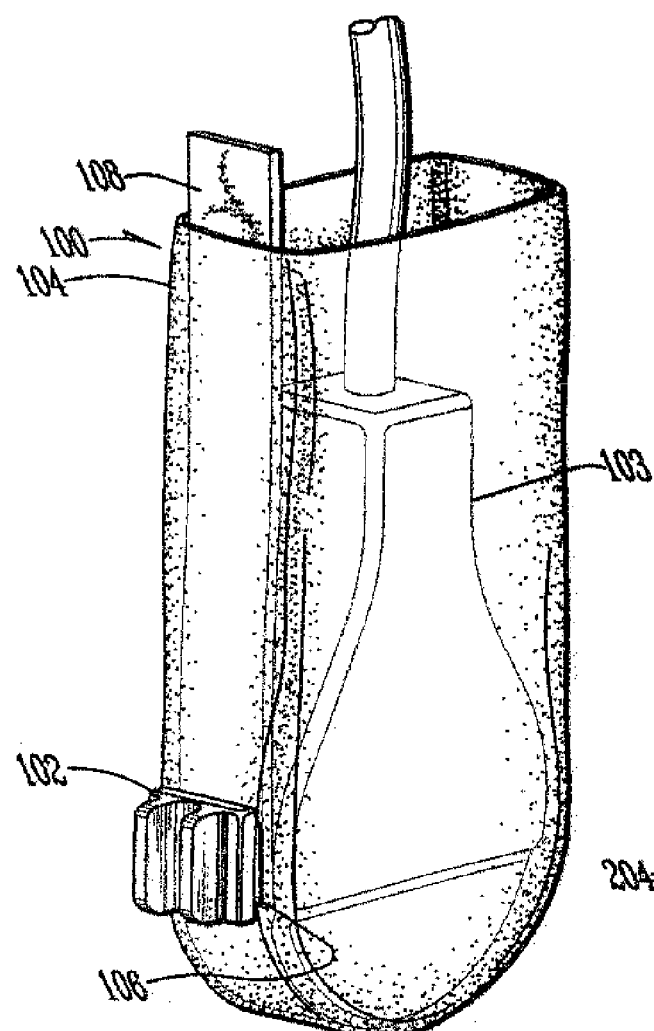
FIG. 1 is a perspective view of the present invention prior to attachment to a transceiver.

Now referring to the drawings wherein like numerals refer to like matter throughout, and more specifically referring to FIG. 1, there is shown a needle guide/transceiver assembly 100 of the present invention, which includes a needle guide 102. Needle guide 102 is coupled to medical imaging device 103, which could be an ultrasound transducer, gamma ray transceiver or other imaging device. Needle guide 102 is preferably a plastic material, such as ABS or equivalent; however, other materials, such as aluminum, surgical steel, and any other suitable material could be substituted. Needle guide 102 is coupled to sterile sheath 104 by exterior adhesive 106. Sterile sheath 104 can be a latex sheath or other material known for use with sheaths and sterile sheaths for medical imaging transceivers. Exterior adhesive 106 can be a contact adhesive applied to sterile sheath 104 or needle guide 102, or it may be adhesive tape. It should be understood that the exterior adhesive 106 can be replaced with an ultrasonic weld or any similar means of attaching matter to a sheath.

Figure 2:
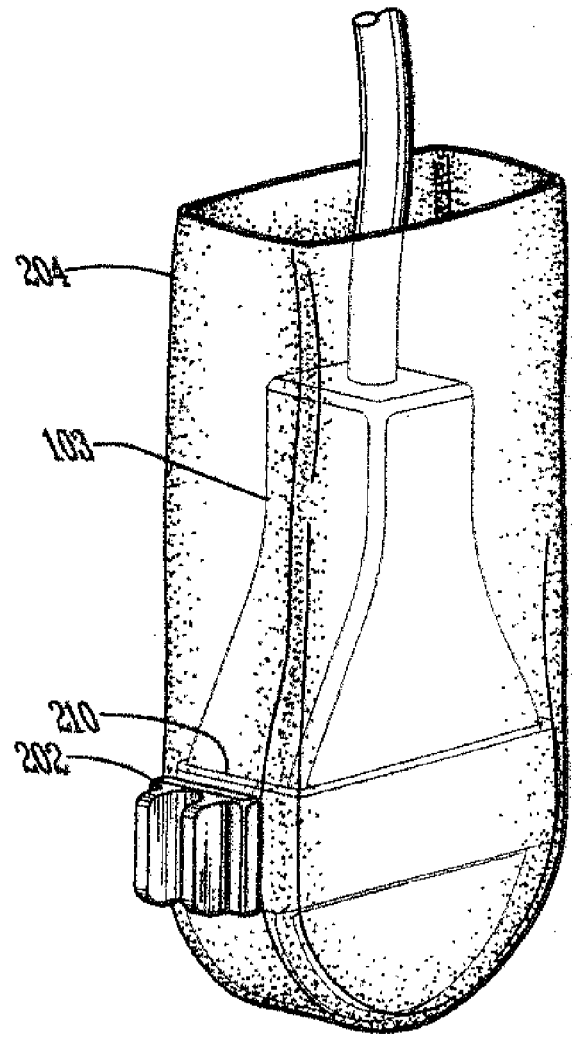
FIG. 2 is a perspective view of an alternate embodiment of the present invention which includes a bracket disposed on the transceiver.

Now referring to FIG. 2, there is shown a needle guide assembly of the present invention, having a needle guide 202 coupled through a sterile sheath 204 to a transceiver mounting bracket 210 disposed on a medical imaging device 103.

Figure 3:
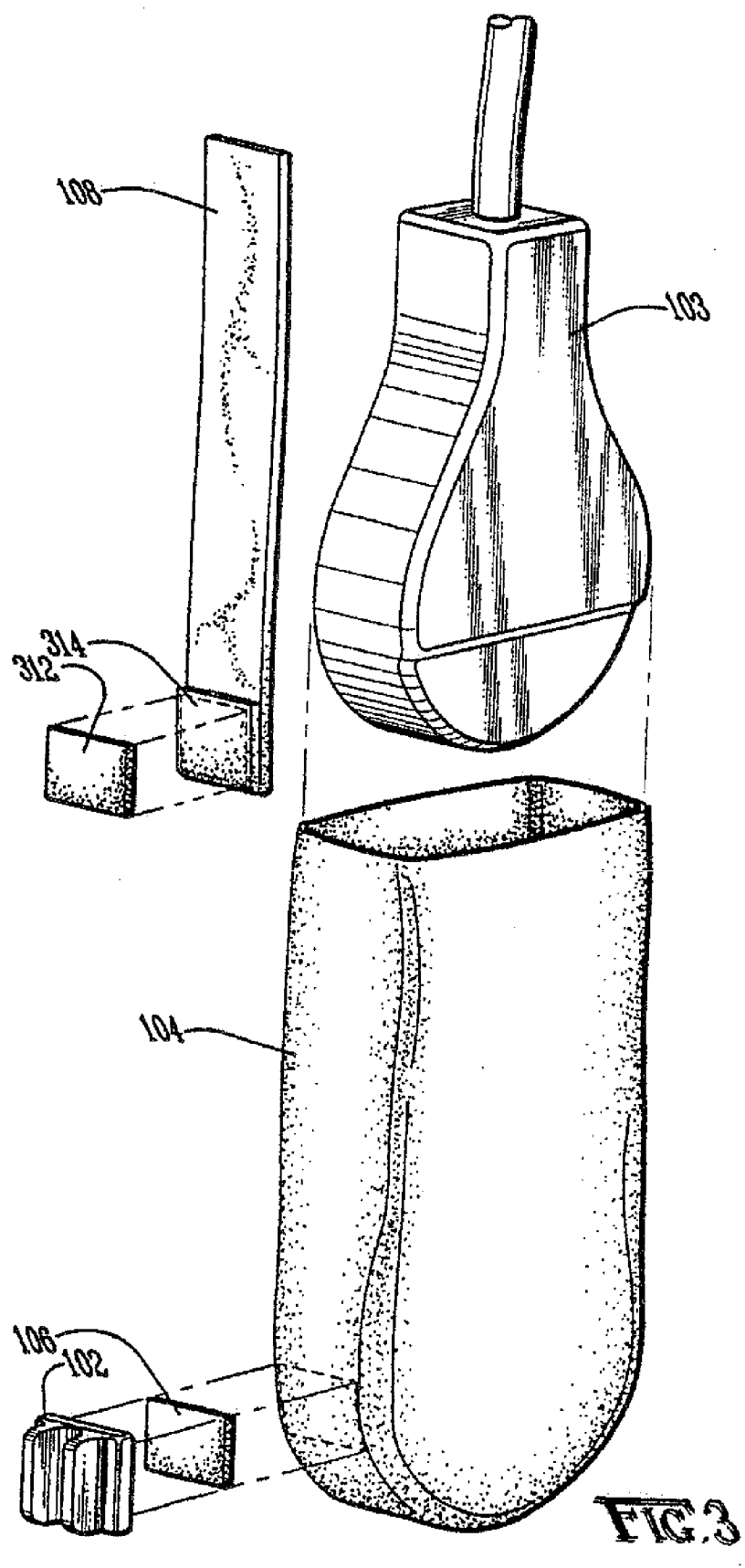
FIG. 3 is a partially exploded perspective view of the apparatus of FIG. 1.

Now referring to FIG. 3, there is shown an exploded view of the needle guide system of FIG. 1, which includes an internal adhesive material 312 disposed on the inside of sterile sheath 104. Internal adhesive material 312 is disposed adjacent to, but on opposing sides of, sterile sheath 104 from exterior adhesive 106. Internal adhesive material 312 is covered by cover for internal adhesive material 314. Cover for internal adhesive material 314 is shown as an integral part of elongated adhesive cover removing pull 108. In a preferred embodiment, elongated adhesive cover removing pull 108 is a strip of material which is folded over at the bottom end to form cover for internal adhesive material 314. It should be understood that cover for internal adhesive material 314 and elongated adhesive cover removing pull 108 need not be integral, nor need they be the same material.

Figure 4:
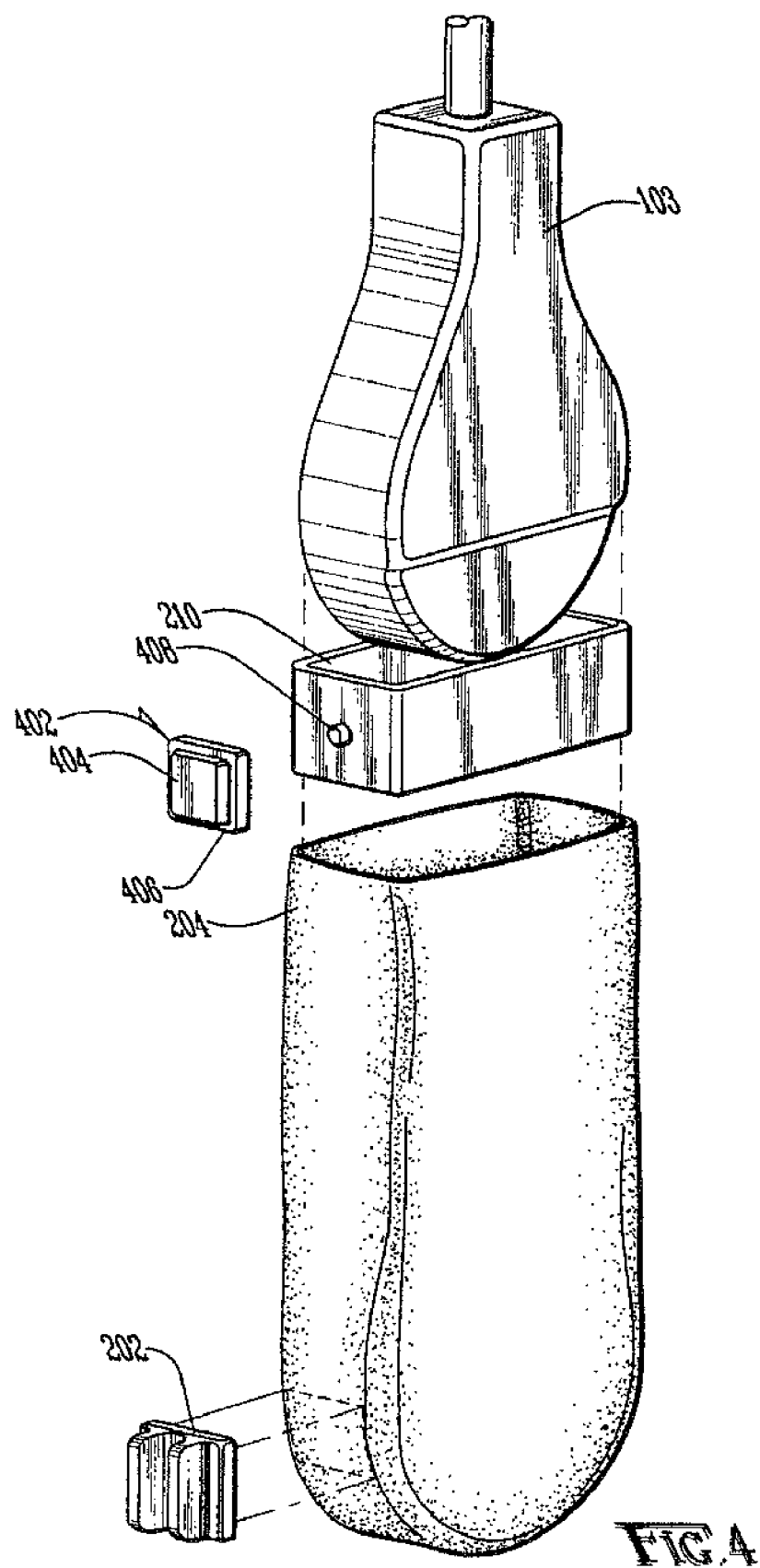
FIG. 4 is a partially exploded perspective view of an alternate embodiment of the needle guide of FIG. 2.

Now referring to FIG. 4, there is shown an adapter 402 having a protruding central portion 404 and non-protruding area 406. Adapter 402 can be attached to sterile sheath 204 in a manner similar to the way needle guide 102 is attached to sterile sheath 104. Adapter 402, after it has been affixed to sterile sheath 204, may be coupled to transceiver mounting bracket 210 by mating with a surface structure 408 disposed on transceiver mounting bracket 210.

In operation, the apparatus and method of the present invention as described and shown in FIGS. 1 and 3, could function as follows:

Medical imaging device 103 is inserted into sterile sheath 104. Elongated adhesive cover removing pull 108 is pulled to expose internal adhesive material 312. Internal adhesive material 312 is then pressed against medical imaging device 103. Needle guide 102, which has been previously attached to sterile sheath 104 via exterior adhesive 106 or other means, can be used for normal clinical activities.

With respect to the embodiment of the present invention shown in FIGS. 2 and 4, the system could function as follows:

Transceiver mounting bracket 210 is mounted on medical imaging device 103. The medical imaging device 103 is inserted into sterile sheath 204. Adapter 402, which has been previously mounted on sterile sheath 204 as discussed above, is mated to surface structure 408. Adapter 402, with its protruding central portion 404 and non-protruding area 406, then can be mated with needle guide 202, thereby coupling needle guide 202 with medical imaging device 103.

Figure 5:
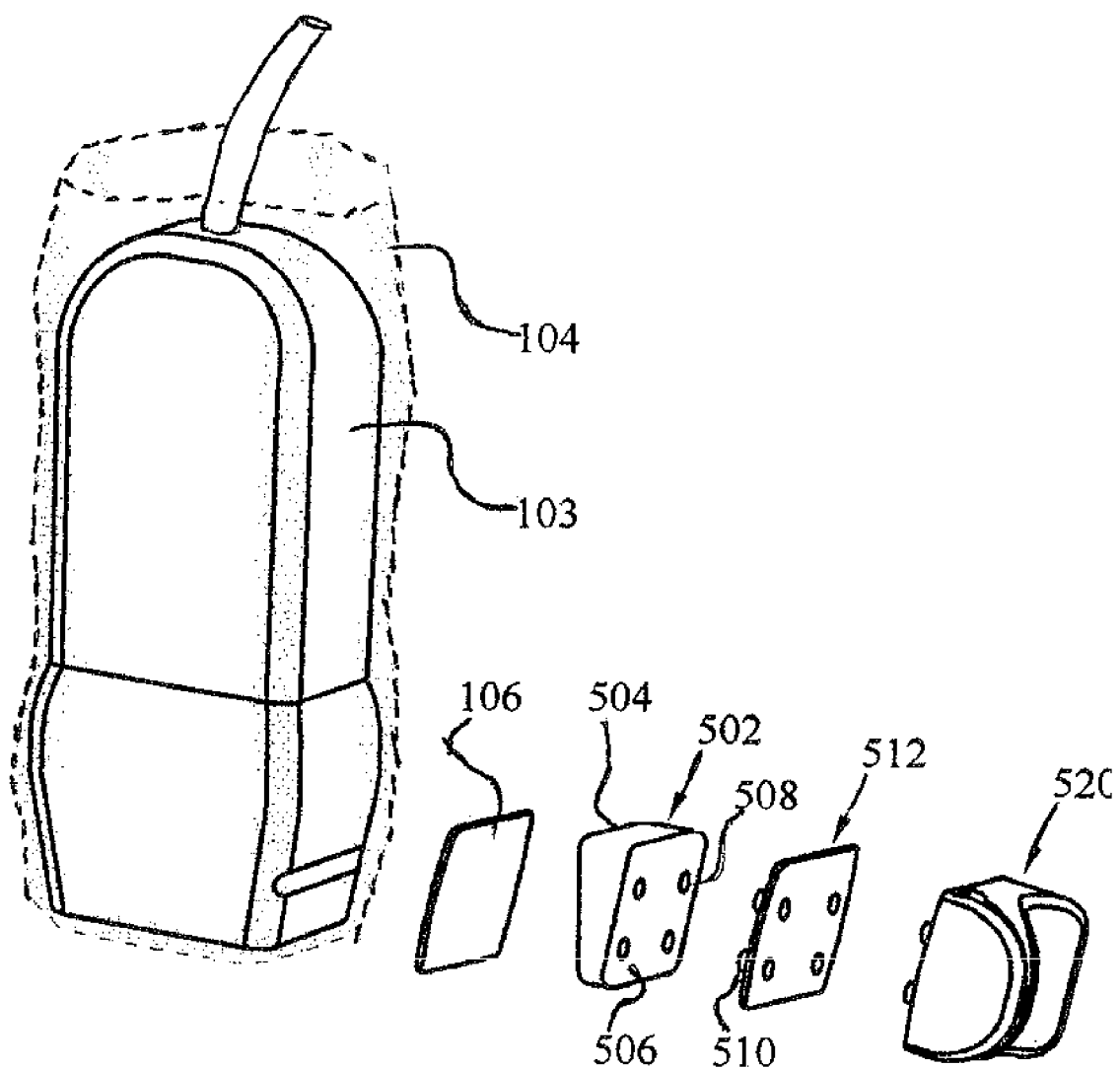
FIG. 5 is an exploded view of a modular attachment mechanism of the present invention.

Now referring to FIG. 5, there is shown an exploded view of an alternate embodiment of the present invention. An attachment 502 is shown coupled to sheath 104 (disposed around device 103) via adhesive 106 similar to FIG. 1. Attachment 502 could be ultrasonically welded to sheath 104 or attached in some other manner. Attachment 502 is not a needle guide. Attachment 502 is an intermediate piece which serves as a platform upon which other devices may be attached. Attachment 502 may be a wedge shape so as to provide for an angular relationship between the needle guide 520 and the device 103. Attachment 502 is shown having an inside surface 504 and an outside surface 506 with a plurality of mating voids 508 therein. Mating voids 508 are configured to mate with mating protuberances 510 on intermediate interlocking attachment 512. Intermediate interlocking attachment 512 is one type of intermediate attachment which could be used to adjust the location or orientation of the needle guide 520. Other types of intermediate interlocking attachments, both angular and non-angular, could be used with varying shapes and dimensions. Intermediate interlocking attachment 512 could be the only such type of device, or it could be one of a series of such interlocking devices disposed between the needle guide 520 and the attachment 502. A combination of angular and non-angular interlocking attachments can be used to change the location and orientation of the needle guide 520. The intermediate interlocking attachment 512 may have voids 508 and protuberances 510 thereon. Needle guide 520 is shown having protuberances 510 thereon as well.

It should be understood that various other ways of connecting intermediate angular and non-angular attachments could be used to change the location and orientation of the needle guide 520 or similar device.

Figure 6:
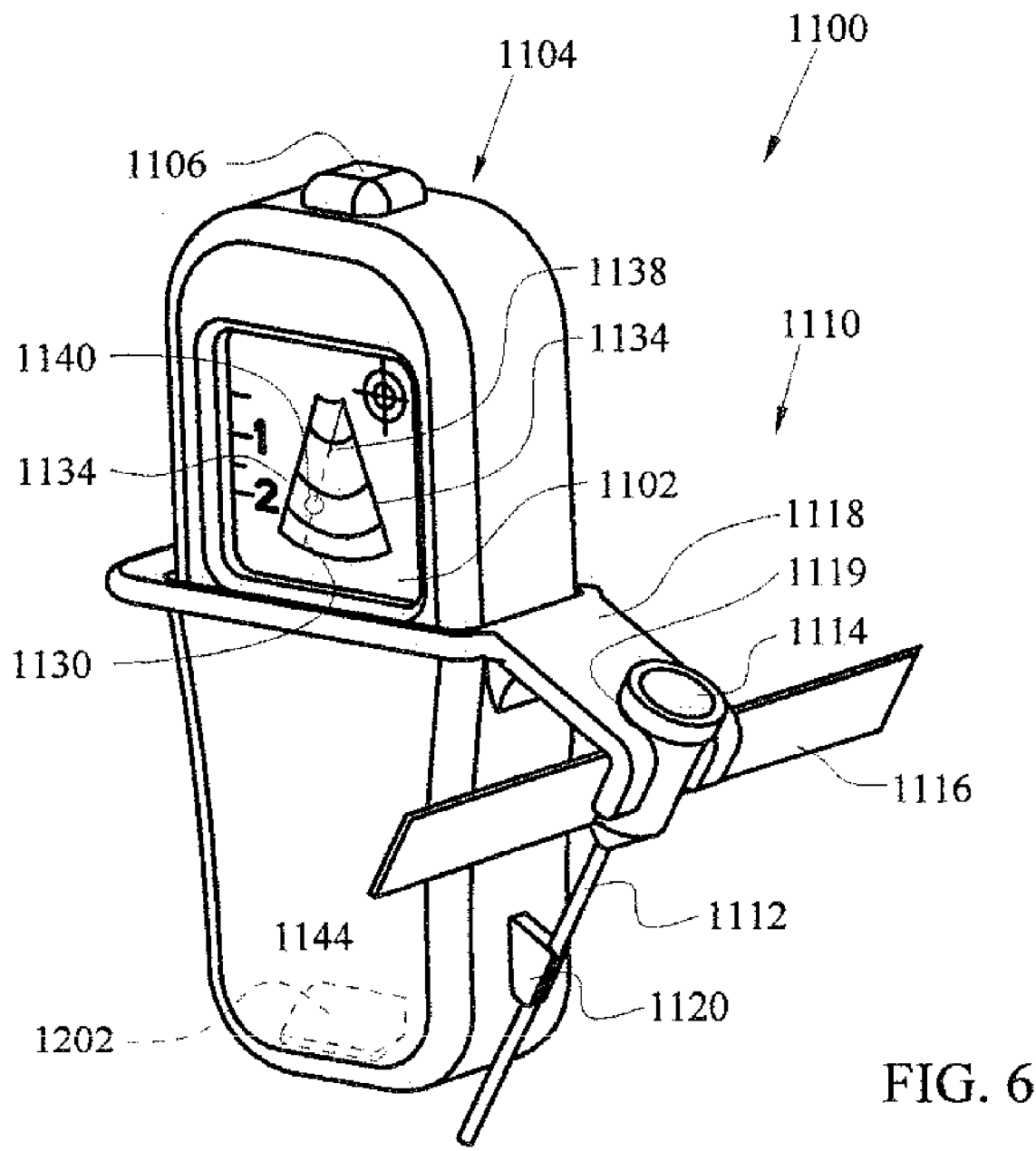
FIG. 6 is a perspective view of the combined handheld medical imaging transceiver system with the semi-rigid sterile imaging cup and integrated introducer system of the present invention.

In FIG. 6, there is shown a medical instrument guiding system of the present invention generally designated 1100. Medical instrument guiding system 1100 includes a low resolution symbol display screen 1102, which may be liquid crystal display or any other suitable display. Low resolution symbol display screen 1102 is described as a low resolution display because it is believed that many of the beneficial aspects of the present invention can be achieved with such a display. It should be understood that the low resolution symbol display screen 1102 could in fact be a high resolution display if it is desired to provide more detailed information.

Similarly, medical instrument guiding system 1100 includes a medical imaging system transceiver section 1104 which could be a low power and low resolution medical imaging transceiver. It should also be understood that while low power and low resolution may be preferable, in some circumstances, high power and high resolution could be used as well.

The term "low power" is used to refer to a medical imaging transmitter which is designed primarily for superficial or relatively small penetration depths into the tissue. The medical imaging systems transceiver section 1104 is described as being low resolution because it is believed that when predetermined symbols are used to display veins, and the location and general orientation of the vein is all that is necessary for the vascular intubation, any additional resolution is not essential.

It is believed that one of the key aspects of the present invention is the realization that the typical high power and high resolution medical imaging devices, with their concomitant relatively large size, price and power consumption, is not essential for assisting in vascular intubation.

In a preferred embodiment, the medical imaging systems transceiver section 1104 has a fixed angle of transmission which produces a scanned area similar to that shown by medical imaging field of view boundary symbol 1134 on the display 1102.

Medical instrument guiding system 1100 includes an introducer system 1110 which includes an introducer catheter section 1112 and an introducer needle receiving section 1114 and comes with introducer adhesive strips 1116 attached thereto for securing the introducer to the patient's skin once the vascular intubation has been successful.

Introducer system 1110 is preferably integrated with the semi-rigid sterile imaging cup 1144, which is shown disposed over the medical imaging system's transceiver section 1104. Introducer system 1110 is held at a constant angle with respect to medical imaging systems transceiver section 1104 by introducer upper guide 1118 and introducer lower guide 1120. Upper guide 1118 is shown having a circular shaped void 1119 therein for receiving the needle receiving section 1114 therein. Introducer upper guide 1118 and introducer lower guide 1120 can be structurally part of the underlying medical imaging systems transceiver section 1104, or they may, as shown, be structurally part of the semi-rigid sterile imaging cup 1144. Of course, a variable angle could be used if desired. Dashed projected needle path symbol 1130 is a representation of the projected path of the introducer system 1110 as it proceeds into the tissue. The medical instrument guiding system 1100 could be configured to display a solid line 1138 or other symbol for the actual introducer catheter section 1112 as it is detected by the medical imaging systems transceiver section 1104.

Low resolution symbol display screen 1102 shows a symbol 1140 which represents the target vein. Here, the symbol 1140 in an exemplary embodiment is not a detailed depiction of the actual vein being intubated. Instead, a simplified standardized view of a vein is displayed. It is believed that in a medical imaging system assisted vascular intubation procedure, it may not be necessary to consider the vein with any more structural specificity than to think of it as a cylinder located and oriented in a particular way at a particular location and depth below the skin. It may even be sufficient to provide information about the location of the cylinder and not its orientation. In other words, in certain situations, it may not even be necessary to provide information regarding the orientation of the cylinder. It is believed that the use of simplified standardized symbols, such as the circular or cylindrical symbol 1140, the projected path 1130, etc., allows the present invention to effectively utilize a display and transceiver combination with lower resolution and, therefore, lower processing requirements and display quality requirements, which often lead to a lower power consumption and lower cost system overall.

In operation, the apparatus of the present invention could be used as follows:

A hand-held medical imaging transceiver 1104 is inserted into a semi-rigid sterile imaging cup 1144, which has disposed in its bottom, a reservoir of gel 1202 which is ruptured when the hand-held medical imaging transceiver 1104 is inserted to the point that a snap or other positive feedback occurs. (In the alternative, gel can be squirted into the semi-rigid sterile imaging cup 1144.)

Top actuator 1106 is depressed to start medical imaging systems transceiver section 1104 and low resolution symbol display screen 1102.

Medical instrument guiding system 1100 is aligned with a vein using visual clues provided on low resolution symbol display screen 1102.

The introducer catheter section 1112 is pushed into the tissue and proceeds along dashed projected needle path symbol 1130 until it contacts the vein. At this point, the solid line 1138 should extend to the target symbol 1140.

At this point, vascular intubation occurs in accordance with known medical procedures. For example, the introducer 1110 is separated from the sterile cup 1144 and laid down so it can be inserted coaxially into the vein. Once the introducer is inserted, the adhesive strips 1116 can be used to hold the introducer in place.

Figure 7:
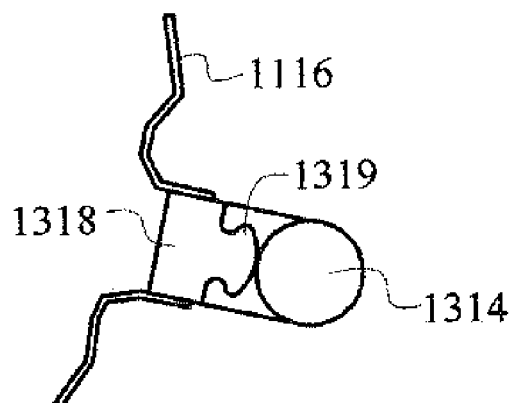
FIG. 7 is an enlarged view of an alternate embodiment of the introducer of the present invention.

Now referring to FIG. 7, there is shown an alternate embodiment of the upper guide 1 section of FIG. 6. Instead of needle receiving section 1114 fitting into a void 1119 as shown in FIG. 6, a void 1319 is associated with the needle receiving section 1314, and the upper guide 1318 mates with the void 1319.

In an exemplary embodiment of the present invention, the adhesive strips 1116 may be stowed away during the initial stages of the vascular intubation process. Once the tipping of the introducer away from the transceiver section 1104 occurs, the adhesive strips 1116 can be deployed. In FIG. 6, adhesive strips are shown in an unfurled configuration. However, during the initial stages of the intubation procedure, they may be folded back and attached to the upper guide 1118.

In FIG. 7, the adhesive strips are shown while they are still stowed next to the upper guide 1318.

Figure 8:
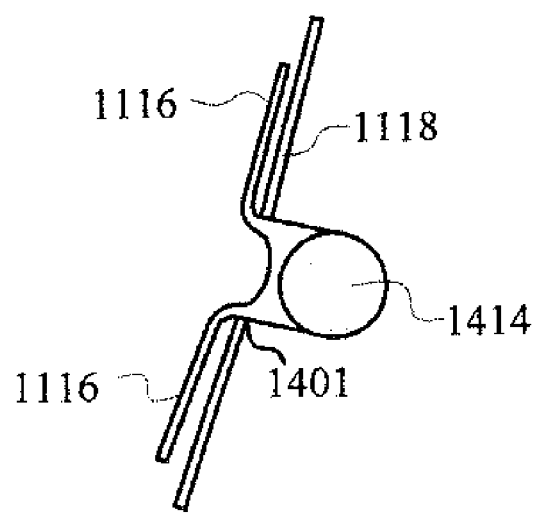
FIG. 8 is a cross-sectional view of an alternate embodiment of the present invention in a stowed position.
Figure 9:
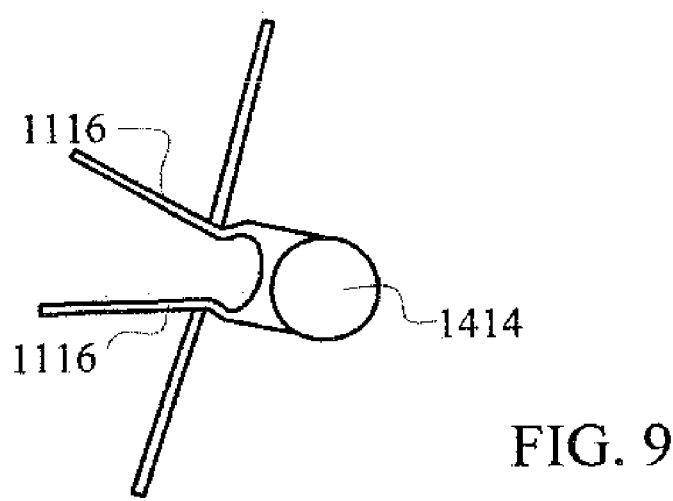
FIG. 9 is a cross-sectional view of the alternate embodiment of FIG. 8 where the introducer has been separated and the adhesive strips are partially removed from a void.

Now referring to FIG. 8, there is shown a view of the adhesive strips 1116 disposed inside a void 1401 in upper guide 1118. FIG. 9 shows the embodiment of FIG. 8 after the needle receiving section 1414 has been separated from the upper guide 1118 and the adhesive strips are partially removed from void 1401.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well, where it is desirable to guide a needle.

While the figures and the detailed description herein are focused upon a general-purpose abdominal transceiver, it is intended that the present invention be read to include within the claims endo-cavity transceivers and any other medical imaging device irrespective of its manner of use.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

What is claimed is:

1. A needle guiding apparatus for use with a medical imaging transceiver, the needle guiding apparatus comprising:
    an elongated generally tubular-shaped sheath having a closed bottom end and an opening at an opposing top end, an interior surface and an exterior surface;
    said sheath not having a medical imaging transceiver disposed therein;
    an angular support member, attached to the exterior surface on an intermediate portion of said sheath at a location on said sheath between said top end and said bottom end;
    a needle guide coupled with said angular support member, said needle guide configured to guide a needle;
    said angular support member configured and positioned to assist in at least indirectly orienting the needle guide into an angular orientation with respect to said medical imaging transceiver when said medical imaging transceiver is later disposed within said sheath;
    an adhesive on an interior surface of said sheath;
    a temporary adhesive cover disposed over said adhesive; and
    means for removal of the temporary adhesive cover.

2. A needle guiding apparatus of claim 1 further comprising an adapter configured for cooperation with a needle guide.

3. A needle guiding apparatus of claim 1 further comprising a needle guide coupled to said sheath.

4. A needle guiding apparatus comprising:
    a sheath having a semi-rigid construction with a closed bottom end and an opening at an opposing top end, an interior surface and an exterior surface;
    said sheath not having a medical imaging transceiver disposed therein;
    said sheath being configured to cover a substantial portion of a bottom half of an integrated handheld medical imaging transceiver with an integral display device for displaying sub-dermal images, and further configured to mate with such integrated handheld medical imaging transceiver such that perceivable feedback is available to indicate mating of said sheath with said integrated handheld medical imaging transceiver;

a first angular support member, attached to the exterior surface on said sheath at a location on said sheath;

a first needle guide coupled with said first angular support member, said first needle guide configured to guide a needle; and said first angular support member configured and positioned to assist in at least indirectly orienting the needle guide into an angular orientation with respect to said integrated handheld medical imaging transceiver when said handheld medical imaging transceiver is later disposed within said sheath.

5. The system of claim 4 wherein said open top end terminates so that said integral display is disposed substantially above the open top end.

6. The system of claim 4 wherein the first angular support member is integrally formed with said sheath.

7. The system of claim 6 further comprising a second angular support member configured to support a second needle guide and further coupled to said sheath and configured and placed to further guide a needle which may be disposed in said first needle guide.

8. The system of claim 7 wherein said second angular support and said second needle guide are integrally formed with said sheath.

9. The system of claim 8 wherein said perceivable feedback is a snap sound.

10. The system of claim 4 wherein said integrated medical imaging transceiver is configured for low power and short penetration depth so as to display near surface sub-dermal vascular matter.

* * * * *